United States Patent [19]

Markley et al.

[11] 4,211,549

[45] Jul. 8, 1980

[54] SUBSTITUTED OXIRANE COMPOUNDS

[75] Inventors: Lowell D. Markley; Elizabeth J. Norton, both of Midland, Mich.

[73] Assignee: The Dow Chemical Company, Midland, Mich.

[21] Appl. No.: 925,487

[22] Filed: Jul. 17, 1978

Related U.S. Application Data

[63] Continuation-in-part of Ser. No. 771,055, Feb. 27, 1977, abandoned, which is a continuation of Ser. No. 638,740, Dec. 8, 1975, abandoned, which is a continuation-in-part of Ser. No. 466,567, May 3, 1974, abandoned.

[51] Int. Cl.$^2$ ............................................. A01N 9/00
[52] U.S. Cl. ..................................... 71/88; 260/348.49
[58] Field of Search ........... 71/88; 260/348.48, 348.49

[56] References Cited

U.S. PATENT DOCUMENTS

| | | | |
|---|---|---|---|
| 3,298,815 | 1/1967 | Mark ........................................ | 71/88 |
| 3,373,011 | 3/1968 | Mussell .................................... | 71/126 |
| 3,476,546 | 11/1969 | Roberts et al. .......................... | 71/88 |
| 3,567,743 | 3/1971 | Anderson ................................ | 71/88 |
| 3,719,465 | 3/1973 | Ozretich .................................. | 71/88 |
| 3,930,835 | 1/1976 | Ozretich .................................. | 71/88 |

FOREIGN PATENT DOCUMENTS 527462  7/1956  Canada ................................. 260/348.48

*Primary Examiner*—Glennon H. Hollrah
*Attorney, Agent, or Firm*—Edward E. Schilling; Ronald G. Brookens

[57] ABSTRACT

Novel substituted oxirane compounds of the formula

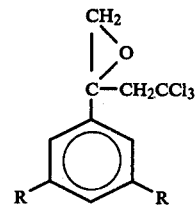

wherein R is Cl, Br or —CH$_3$ are useful as herbicidal agents useful in the control of green foxtail in the presence of corn, sorghum and soybeans.

15 Claims, No Drawings

SUBSTITUTED OXIRANE COMPOUNDS

CROSS-REFERENCE TO RELATED APPLICATIONS

This application is a continuation-in-part of our co-pending application, Ser. No. 771,055 filed Feb. 27, 1977, and now abandoned, which is in turn a continuation of our earlier application, Ser. No. 638,740, filed Dec. 8, 1975, and now abandoned, which is in turn a continuation-in-part of our still earlier application, Ser. No. 466,567, filed May 3, 1974, and now abandoned.

BACKGROUND OF THE INVENTION

1. Field of the Invention

The invention relates to novel herbicidal epoxy butanes useful in the control of green foxtail, *Setaria viridis*, a commercially significant weed in the cornbelt of the U.S.A. Other herbicides have been discovered which are inherently capable of controlling green foxtail selectively in the presence of corn, soybeans and sorghum, but certainly none capable of such control on an economically feasible cost basis.

2. Description of the Prior Art

Epoxy butanes, or oxiranes, have been disclosed in Canadian Pat. No. 527,462, but not taught as herbicides. Certain substituted alpha-methyl styrenes have been disclosed broadly as herbicides, U.S. Pat. No. 3,373,011. Such compounds can be epoxidized to produce the present type of oxirane compound. An oxirane having an unsubstituted phenyl ring on the butane chain and the herbicidal properties thereof are taught in U.S. Pat. No. 3,719,465. Oxiranes homologous to these having halogen or alkyl substituents in the 3, 4 or 3 and 4 ring positions and their herbicidal properties are taught and claimed in U.S. Pat. No. 3,930,835. This latter patent teaches selectivity of herbicidal control of grassy weeds, including yellow foxtail, in the presence of grassy crops such as corn and rice, but highly effective and economical and selective control of green foxtail in the presence of corn, soybeans and sorghum is not taught.

SUMMARY OF THE INVENTION

The present invention is directed to novel substituted oxirane compounds of the following formula:

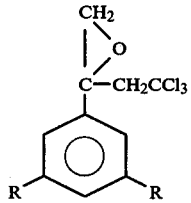

(I)

wherein each R group independently represents bromo, chloro or methyl.

The compounds of the above Formula I, hereinafter referred for convenience as "active ingredients", have been found to be uniquely active as herbicides in the control of green foxtail in the presence of corn, soybeans or sorghum. Accordingly, the present invention also encompasses compositions containing one or more active ingredients as well as methods of controlling green foxtail. Such methods comprise applying a herbicidal effective amount of one or more active ingredients preemergently or early postemergently to the locus of the undesired plants, and particularly to the locus where the valuable crop is to germinate and grow.

DETAILED DESCRIPTION

The term "herbicide" is used herein to mean an active ingredient which controls or modifies the growth of plants. By "growth controlling" or "herbicidally-effective" amount is meant an amount of active ingredient which causes a modifying effect and includes deviations from natural development, killing, regulation, dessication, retardation, and the like. The term "plants" is meant to include germinant seeds, emerging seedlings and established vegetation.

The active ingredients of the present invention are generally oils or crystalline solids at ambient temperatures which are soluble in many organic solvents commonly employed as herbicidal carriers. The active ingredients of the above Formula I wherein each R is chloro constitute a preferred embodiment of the present invention. Active ingredients wherein each R group is the same constitute a further preferred embodiment. Another preferred embodiment of the present invention includes active ingredients wherein each R group is bromo. In still another embodiment of the present invention, active ingredients wherein each R group is methyl are preferred.

The active ingredients of the above Formula I are readily prepared by the reaction of a substituted styrene compound of the formula:

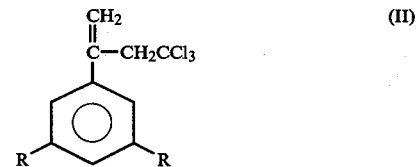

(II)

wherein R is as previously defined, with a suitable percarboxylic acid reactant. Representative and suitable percarboxylic acids which can be employed in the preparation of the active ingredients include, for example, chloracetic acid, trifluoroacetic acid, perbenzoic acid, paracetic acid, and the like. In the present invention, buffer solutions of the acid reactants are preferably employed and are prepared by the use of a buffer agent, such as, for example, sodium acetate, sodium benzoate, and the like.

In carrying out the reaction, the substituted styrene reactant of Formula II is usually mixed with a carrier medium, such as, for example, methylene chloride, chloroform, 1,2-dichlorobenzene and the like, and mixed slowly with the percarboxylic acid reactant in a buffer solution. While the amounts of the reactants to be employed are not critical, the reaction generally consumes reactants in the proportion of 1 mole of substituted styrene reactant to one or more moles of percarboxylic acid reactant. A suitable ratio of reactants is from about 1 to 1 to about 1 to 6 (substituted styrene:percarboxylic acid) and the employment of the reactant in a mole ratio of from about 1 to 3 moles preferred. The reaction is usually conducted at temperatures between about 20° and 40° C. and is ordinarily carried out at ambient atmospheric pressure. The resulting reaction mixture is usually maintained, with stirring, for a period of time sufficient to provide for substantial completion of the reaction. Generally, the reaction mixture is stirred at ambient temperatures for a period of from about 24 to about 100 hours or more. Recovery of the desired product from the reaction mixture is achieved by employing conventional procedures. Typically, the reaction mass is washed with water and neutralized with a sufficient amount of a base, e.g., sodium carbonate or the like, before being concentrated to dryness under subatmospheric pressure.

The following examples illustrate the present invention and the manner by which it can be practiced but, as such, are not to be construed as limitations upon the overall scope of the same.

EXAMPLE 1

2-(3,5-dichlorophenyl)-4,4,4-trichloro-1-butene (39.7 grams; 0.13 mole) was mixed with about 225 milliliters (ml.) of methylene chloride. A solution of 40% peracetic acid (74 grams; 0.39 mole) in 5.3 grams of sodium acetate trihydrate was then added dropwise to the butene reactant solution. During the addition of the peracetic acid solution, the temperature of the reaction mixture rose from about 23° to about 28° C. The resulting reaction mixture was maintained, with stirring, for a period of about 100 hours at ambient temperatures. Following this period, the reaction mixture was washed with 3-200 milliliter portions of a 10% sodium carbonate solution. The organic product layer was separated and washed with another 100 milliliter portion of water and then dried over anhydrous sodium sulfate. The organic product layer was then reduced in vacuo. The resulting yellow residue was mixed with 230 ml. of methylene chloride and the resulting mixture washed with 2-100 milliliter portions of a 10% sodium carbonate solution. The organic product layer was separated therefrom and dried over sodium sulfate and again reduced in vacuo at 30° C. and at 0.1 millimeter of mercury. As a result of such operations, the desired 2-(3,5-dichlorophenyl)-2-(2,2,2-trichloroethyl)-oxirane product was recovered as a yellow oil having a refractive index $n_D^{25} = 1.5720$. Infrared and nuclear magnetic reasonance spectra were consistent with the assigned structure.

Other active ingredients of the present invention are similarly prepared by employing procedures analogous to those set forth in the above example and the foregoing teachings of the specification by reacting a selected substituted styrene reactant of Formula II with a percarboxylic acid.

Such other active ingredients included are:

2-(3,5-dimethylphenyl)-2-(2,2,2-trichloroethyl)-oxirane, as a light yellow oil having a refractive index $n_D^{25} = 1.5441$ and 2-(3,5-dibromophenyl)-2-(2,2,2-trichloroethyl)oxirane, as a light yellow oil having a refractive index $n_D^{25} = 1.6022$ and each having the composition and structure thereof confirmed by elemental analysis and infrared and nuclear magnetic reasonance spectra.

The compounds of the present invention have been found to be suitable for use in methods for the preemergent and early postemergent control of green foxtail, i.e., *Setaria viridis*, in the presence of the seeds or seedling plants of corn, soybeans and sorghum. For such use, unmodified active ingredients of the present invention can be employed. However, the present invention embraces the use of a herbicidally-effective amount of the active ingredients in composition form with an inert material known in the art as an adjuvant or carrier in solid or liquid form. Thus, for example, an active ingredient can be dispersed on a finely divided solid and employed therein as a dust. Also, the active ingredients, as liquid concentrates or solid compositions comprising one or more of the active ingredients, can be dispersed in water, typically with the aid of a wetting agent, and the resulting aqueous dispersion employed as a spray. In other procedures, the active ingredient can be employed as a constituent of organic liquid compositions, oil-in-water and water-in-oil emulsions, or water dispersions, with or without the addition of wetting, dispersion, or emulsifying agents.

Suitable adjuvants of the foregoing type are well known to those skilled in the art. The methods of applying the solid or liquid herbicidal formulations similarly are well known to the skilled artisan.

As organic solvents used as extending atents there can be employed hydrocarbons, e.g. benzene, toluene, xylene, kerosene, diesel fuel, fuel oil, and petroleum naphtha, ketones such as acetone, methyl ethyl ketone and cyclohexanone, chlorinated hydrocarbons such as carbon tetrachloride, chloroform, trichloroethylene, and perchloroethylene, esters such as ethyl acetate, amyl acetate and butyl acetate, ethers, e.g., ethylene glycol monomethyl ether and diethylene glycol monomethyl ether, alcohols, e.g., methanol, ethanol, isopropanol, amyl alcohol, ethylene glycol, propylene glycol, butyl Carbitol acetate and glycerine. Mixtures of water and organic solvents, either as solutions or emulsions, can be employed.

The active ingredients can also be applied as aerosols, e.g., by dispersing them by means of a compressed gas such as dichlorodifluoromethane or trichlorofluoromethane and other Freons and Genetrons, for example.

The active ingredients of the present invention can also be applied with solid adjuvants or carriers such as talc, pyrophyllite, synthetic fine silica, attapulgus clay, kieselguhr, chalk, diatomaceous earth, lime, calcium carbonate, bentonite, fuller's earth, cottonseed hulls, wheat flour, soybean flour, pumice, tripoli, wood flour, walnut shell flour, redwood flour and lignin.

As stated, it is frequently desirable to incorporate a surface active agent in the compositions of the present invention. Such surface active or wetting agents are advantageously employed in both the solid and liquid compositions. The surface active agent can be anionic, cationic or nonionic in character.

Typical classes of surface active agents include alkyl sulfonate salts, alkylaryl sulfonate salts, alkylaryl polyether alcohols, fatty acid esters of polyhydric alcohols and the alkylene oxide addition products of such esters, and addition products of long chain mercaptans and alkylene oxides. Typical examples of such surface active agents include the sodium alkylbenzene sulfonates having 10 to 18 carbon atoms in the alkyl group, alkylphenol ethylene oxide condensation products, e.g., p-isooctylphenol condensed with 10 ethylene oxide units, soaps, e.g., sodium stearate and potassium oleate, sodium salt of propylnaphthalene sulfonic acid, di(2-ethylhexyl)-ester of sodium sulfosuccinic acid, sodium lauryl sulfate, sodium decane sulfonate, sodium salt of the sulfonated monoglyceride of coconut fatty acids, sorbitan sesquioleate, lauryl trimethyl ammonium chloride, octadecyl trimethyl ammonium chloride, polyethylene glycol lauryl ether, polyethylene glycol esters of fatty acids and rosin acids, e.g., Ethofat 7 and 13, sodium N-methyl-N-oleyl taurate, Turkey Red Oil, sodium dibutyl naphthalene sulfonate, sodium lignin sulfonate, polyethylene glycol stearate, sodium dodecylbenzene sulfonate, tertiary dodecyl polyethylene glycol thioether (nonionic 218), long chain ethylene oxide-propylene oxide condensation products, e.g., Pluronic 61 (molecular weight 1000), polyethylene glycol ester of tall oil acids, sodium octyl phenoxyethoxyethyl sulfate, tris(polyoxyethylene)-sorbitan monostearate (Tween 60), and sodium dihexyl sulfosuccinate.

The concentration of the active ingredients in solid or liquid compositions generally is from about 0.003 to about 95 percent by weight or more. Concentrations of from about 0.003 to about 50 weight percent are often employed. In compositions to be employed as concentrates, the active ingredient can be present in a concentration of from about 5 to about 98 weight percent. The active ingredient compositions can also contain other compatible additaments, for example, phytotoxicants, plant growth regulants, pesticides and the like and can be formulated with solid particulate fertilizer carriers such as ammonium nitrate, urea and the like.

The present compositions can be applied by the use of power-dusters, boom and hand sprayers, spray-dusters, by addition to irrigation water, and by other conventional means. The compositions can also be applied from airplanes as a dust or a spray since certain of the active ingredients are effective at low application rates.

The exact rate to be applied is dependent not only upon the specific active ingredient being employed, but also upon the stage of growth thereof as well as the part of the green foxtail plants to be contacted with the toxic active ingredient. Thus, it is to be understood that all of the active ingredients of the invention and compositions containing the same may not be equally effective at similar concentrations. In selective pre- and early post-emergence operations, a dosage of from about 0.13 to about 4 pounds per acre is usually employed but about 1 to about 2 pounds per acre is a preferred rate. In view of the foregoing and following disclosures, one skilled in the art can readily determine the optimum rate to be applied in any particular case.

In an illustrative representative operation, each compound to be utilized in a series of test is dissolved in acetone to one half of the final volume (twice the final concentration) to be used and the acetone solution in each case is admixed with an equal volume of water containing 0.1 percent by weight of Tween-20 surface active material (Tween-20 is a trademark of Atlas Chemical Company). Each compound is selected from a group consisting of compounds according to the invention as well as prior art compounds and another compound closely related to one of the prior art compounds. The compositions, generally in the nature of an emulsion, are employed to treat separate respective seed beds of sandy loam soil of good nutrient content wherein each seed bed contains separate groups of a known number of good, viable corn seeds. The various beds are positioned side by side and exposed to substantially identical conditions of temperature and light. Each bed is maintained so as to prevent any interaction with test compounds in different seed beds. Each seed bed is treated with one of the compositions as a soil drench applied uniformly throughout the surface of the bed at one of two predetermined amounts of a given test compound. The compositions are applied so that respectively different seed beds are treated with one of each of the test compounds. Another seed bed is treated only with water to serve as a control. After treatment, the seed beds are maintained for two weeks under greenhouse conditions conductive for good plant growth and watered as necessary. The specific plant species, test compound and dosage and the percent control obtained are set forth in Table 1 below. Control refers to the reduction in growth compared to the observed results of the controls.

Table 1

| Compound Under Test | Dosage in Lbs. per Acre | Corn |
|---|---|---|
| Comparisons | | |
| A | 1 | 90 |
| A | 0.5 | 60 |
| B | 1 | 60 |
| B | 0.5 | 35 |
| C | 1 | 50 |
| C | 0.5 | 25 |
| Compound of the invention | | |
| D | 1 | 30 |
| D | 0.5 | 0 |

A = 2-phenyl-2-(2,2,2-trichloroethyl)oxirane
B = 2-(3-chlorophenyl)-2-(2,2,2-trichloroethyl)oxirane
C = 2-(4-chlorophenyl)-2-(2,2,2-trichloroethyl)oxirane
D = 2-(3,5-dimethylphenyl)-2-(2,2,2-trichloroethyl)oxirane The test results shows that the compound of the invention identified in the Table as D shows little or no control of corn (maize). In contrast, the compounds identified as A, B and C show moderate to complete control of corn.

In yet additional preemergence operations carried out in a fashion similar to the above but with application of test compounds and comparison compounds at two or more dosage levels in respective seedbeds, computations were made by probit analysis, utilizing the test results, to show the dosage rate needed for 80% control of *Setaria viridis*. The calculated dosage rates are tabulated in Table 2.

Table 2

Activity of Substituted Oxiranes to *Setaria viridis*

| Ring Substituents (other than hydrogen) | | | Dosage Rate for 80% |
|---|---|---|---|
| X | Y | Z | Control Lbs./A. |
| — | — | — | >4 |
| Cl | — | — | >4 |
| — | Cl | — | >8 |
| *Cl | — | Cl | 0.3 |
| CH$_3$ | — | — | >4 |
| *CH$_3$ | — | CH$_3$ | 0.1 |
| C$_2$H$_5$ | — | — | >4 |

*Compound of the invention

In field tests showing the marked selectivity of 2-(3,5-dichlorophenyl)-2-(2,2,2-trichloroethyl)oxirane toward corn, test plots, which had been treated with compound, as well as untreated plots, were seeded throughout with corn. The dosage rates used and the percent control observed are listed as follows in Table 3.

Table 3

Preemergent Activity of 2-(3,5-dichlorophenyl)-2-(2,2,2-trichloroethyl)oxirane

| Dosage Rate Lbs./A. | % Control Corn |
| --- | --- |
| 0.5 | 0 |
| 1 | 0 |

In additional operations illustrating the invention separate aqueous compositions containing, respectively, comparison compounds 2-(m-bromophenyl)-2-(2,2,2-trichloroethyl)oxirane; 2-(m-nitrophenyl)-2-(2,2,2-trichloroethyl)-oxirane; 2-(m-trifluoromethyl(phenyl))-2-(2,2,2-trichloroethyl)oxirane; 2-(m-ethoxyphenyl)-2-(2,2,2-trichloroethyl)-oxirane; 2-(m-benzyloxyphenyl)-2-(2,2,2-trichloroethyl)oxirane; and 2-(3,4-dichlorophenyl)-2-(2,2,2-trichloroethyl)oxirane; and a compound of the invention: 2-(3,5-dichlorophenyl)-2-(2,2,2-trichloroethyl)oxirane were prepared as follows:

Each compound to be utilized in the tests was dissolved in acetone to one-half of the final volume (twice the final concentration) to be used and the acetone solution in each case was admixed with an equal volume of water containing 0.2 percent by weight surface active agent (Tween 20).

The aqueous compositions, generally in the nature of an emulsion, were then employed for the treatment of respective seedbeds of good agricultural soil which had been prepared in pots and some seeded with corn (*Zea mays*) and some with the seeds of green foxtail (*Setaria viridis*). In the treating operations, each of a series of predetermined quantities of each of the compositions was applied to replicate seedbeds and watered in according to normal germinating practices. The quantities were controlled to supply a substantially uniform dosage in respective seedbeds equivalent to 1/16, ⅛, ¼, ½, 1, 2 and 4 pounds of the oxirane compound per acre. Other seedbeds were similarly seeded with the named plant species but were left untreated to serve as checks.

After about 2 weeks under greenhouse conditions conducive for good plant germination and growth, the seedbeds were examined to ascertain what control of the growth of seeds had been obtained. The results are set forth in the following Table 4, the compound being identified by the ring substitution.

same selectivity is shown while any seeded green foxtail tested concurrently is controlled.

Substantially the same fine results are obtained upon applying any of the three compounds set forth above at a dosage in the range of about 0.13 to about 2 pounds per acre upon seedling corn, seedling sorghum and seedling soybeans as well as seedling green foxtail, whereupon the green foxtail is effectively and selectively controlled in an early postemergence operation.

The substituted styrene reactants of Formula II and the percarboxylic acids employed as starting materials in the preparation of the active ingredients of the present invention are known and are readily available or can be easily prepared by those skilled in the art according to known methods or methods analagous thereto.

It is obvious that various ramifications and modifications of the instant invention can be made in light of the foregoing disclosure.

What is claimed is:

1. A compound of the formula

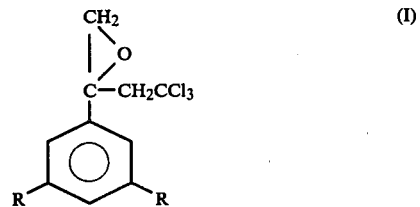

wherein each R group represents bromo, chloro or methyl.

2. The compound according to claim 1 which is 2-(3,5-dichlorophenyl)-2-(2,2,2-trichloroethyl)oxirane.

3. The compound according to claim 1 which is 2-(3,5-dimethylphenyl)-2-(2,2,2-trichloroethyl)oxirane.

4. The compound according to claim 1 which is 2-(3,5-dibromophenyl-2-(2,2,2-trichloroethyl)oxirane.

5. A composition comprising an inert carrier and a herbicidally-effective amount of compound of the formula

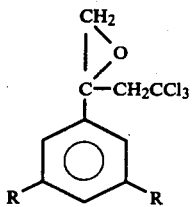

TABLE 4

% Preemergent Control of Corn and Green Foxtail (g.f.)

| Dosage Rage, lb./acre | Ring Substitution | | | | | | | |
| --- | --- | --- | --- | --- | --- | --- | --- | --- |
| | m-bromo | m-nitro | m-methoxy | m-ethoxy | m-benzyloxy | m-CF$_3$ | 3,4-dichloro | 3,5-dichloro |
| | corn g.f. | corn g.f. | corn g.f. | corn g.f. | corn g.f. | corn g.f. | corn g.f. | corn g.f. |
| 4 | 0  20 | 50  98 | 60  98 | 70  30 | 0  0 | 95  90 | 50  60 | 0  100 |
| 2 | 0  0 | 20  95 | 50  95 | 30  20 | 0  0 | 70  50 | 30  20 | 0  100 |
| 1 | 0  0 | 0  80 | 30  85 | 10  10 | 0  0 | 50  50 | 0  10 | 0  95 |
| 0.5 | 0  0 | 0  60 | 0  60 | 0  0 | 0  0 | 0  40 | 0  0 | 0  90 |
| .25 | 0  0 | 0  10 | 0  30 | 0  0 | 0  0 | 0  50 | 0  0 | 0  70 |
| .125 | 0  0 | 0  0 | 0  0 | 0  0 | 0  0 | 0  20 | 0  0 | 0  80 |
| .062 | 0  0 | 0  0 | 0  0 | 0  0 | 0  0 | 0  0 | 0  0 | 0  60 |

On repeating the herbicidal tests substantially as set forth above with 2-(3,5-dibromophenyl)-2-(2,2,2-trichloroethyl)oxirane and 2-(3,5-dimethylphenyl)-2-(2,2,2-trichloroethyl)oxirane, respectively, in place of 2-(3,5-dichlorophenyl)oxirane, and upon seeded soybeans and sorghum in place of corn, substantially the wherein each R group represents bromo, chloro or methyl.

6. The composition according to claim 5 wherein the compound is 2-(3,5-dichlorophenyl)-2-(2,2,2-trichloroethyl)oxirane.

7. The composition according to claim 5 wherein the compound is 2-(3,5-dimethylphenyl)-2-(2,2,2-trichloroethyl)oxirane.

8. The composition according to claim 5 wherein the compound is 2-(3,5-dibromophenyl)-2-(2,2,2-trichloroethyl)oxirane.

9. The method of controlling green foxtail in the presence of corn, soybeans or sorghum which comprises applying to the locus of said plants a herbicidally-effective amount of a compound of the formula

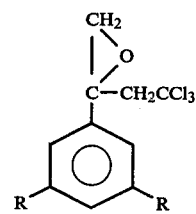

wherein each R group represents bromo, chloro or methyl without substantial phytotoxic effect on the corn, soybeans or sorghum.

10. The method of claim 9 wherein the compound is 2-(3,5-dichlorophenyl)-2-(2,2,2-trichloroethyl)oxirane.

11. The method of claim 9 wherein the compound is 2-(3,5-dimethylphenyl)-2-(2,2,2-trichloroethyl)oxirane.

12. The method of claim 9 wherein the compound is 2-(3,5-dibromophenyl)-2-(2,2,2-trichloroethyl)oxirane.

13. The method of claim 9 wherein the compound is applied to green foxtail preemergently in the presence of corn.

14. The method of claim 9 wherein the compound is applied to green foxtail early postemergence in the presence of corn.

15. The method as in claim 13 or 14 in which the compound is applied at a dosage rate in the range of about 1 to about 2 pounds per acre.

* * * * *